United States Patent [19]

Fry

[11] Patent Number: 5,280,797

[45] Date of Patent: Jan. 25, 1994

[54] DENTAL FLOSS TOOL

[76] Inventor: Stephen Fry, 5206 E. Via Buena Vista, Paradise Valley, Ariz. 85253

[21] Appl. No.: 8,484

[22] Filed: Jan. 25, 1993

[51] Int. Cl.⁵ .......................................... A61C 15/00
[52] U.S. Cl. ..................................... 132/323; 132/325
[58] Field of Search ............... 132/323, 324, 326, 327, 132/325

[56] References Cited

U.S. PATENT DOCUMENTS

| | | | |
|---|---|---|---|
| 1,644,390 | 10/1927 | Miller | 132/323 |
| 1,990,404 | 2/1935 | Doner | 132/326 |
| 2,113,439 | 4/1938 | Bean | 132/326 |
| 2,735,436 | 2/1956 | Russo | 132/323 |
| 2,756,758 | 7/1956 | Segerblom | 132/326 |
| 2,828,754 | 4/1958 | Stewart | 132/323 |
| 3,858,594 | 1/1975 | Ensminger | 132/325 |
| 4,041,962 | 8/1977 | Johansson et al. | 132/323 |
| 4,052,994 | 10/1977 | Thun | 132/325 |
| 4,727,895 | 3/1988 | Berarducci | 132/323 |
| 4,738,271 | 4/1988 | Bianco | 132/323 |
| 5,029,593 | 7/1991 | Huttunen | 132/323 |
| 5,105,840 | 4/1992 | Giaropuzzi | 132/325 |

FOREIGN PATENT DOCUMENTS 2503861  8/1976  Fed. Rep. of Germany ...... 132/324

Primary Examiner—Gene Mancene
Assistant Examiner—Frank A. Laviola
Attorney, Agent, or Firm—LaValle D. Ptak

[57] ABSTRACT

A dental floss tool has a short flat handle in a first plane, with a floss winding post extending from the upper surface thereof. Extending downwardly from the lower surface are a pair of spaced legs attached to the handle at one end and spaced apart from one another at the opposite end thereof. Guide grooves are placed on the legs for guiding dental floss from the winding post to the end of the first or outermost leg, back to the second leg, and then upwardly through a hole in the handle located between the winding post and the second leg, back to the winding post. The floss, which extends from the lower end of the second leg through the hole, then may be engaged by the thumb of the user to adjust the tension of the floss extending between the ends of the two legs.

7 Claims, 1 Drawing Sheet

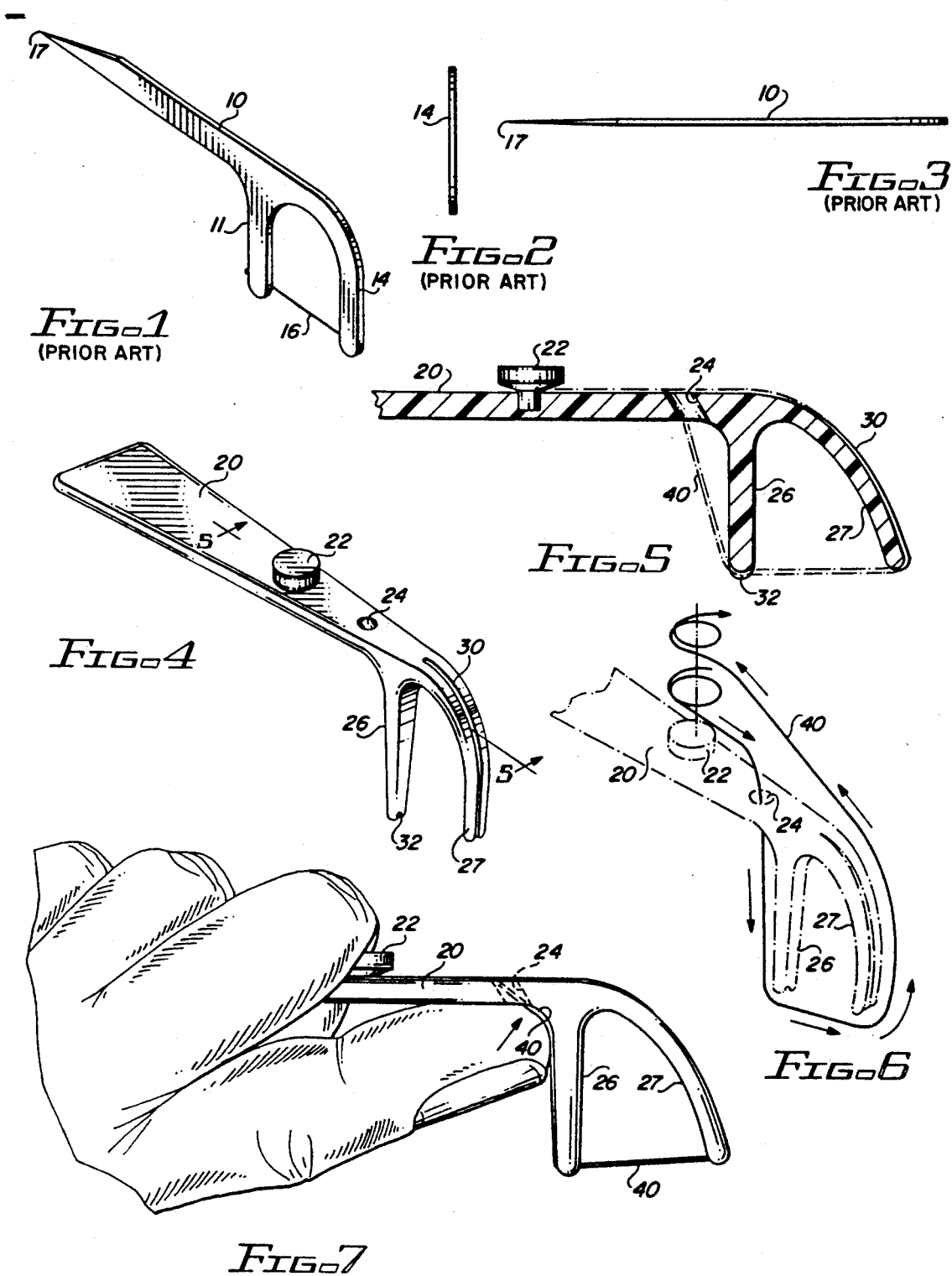

DENTAL FLOSS TOOL

BACKGROUND

Dentists recommend using dental floss after each meal, or at least daily, to clean between teeth to fight placque buildup and to stimulate the growth of strong and healthy gums. Placque is a leading cause of tooth decay, gum disease and bad breath. Food particles frequently become lodged between the teeth, and placque builds up between the teeth in regions where a toothbrush cannot reach. This buildup between the teeth increases the danger of infection of the gums and tooth decay.

Typically, dental floss is wrapped around a finger on each hand, with the person then sticking his or her fingers in the mouth to effect the flossing. Many persons, however, dislike flossing their teeth in this manner.

To overcome the disadvantages of wrapping floss around the fingers to accomplish flossing of teeth, various flossing tools have been developed. One such tool is a disposable handle with a pair of spaced legs on one end forming a U-shaped extension. In this tool, a short strip of floss is molded into the ends of the two legs across the space forming the U-shaped end. The floss in this tool is not removable; so that if it should become caught between the teeth, it is necessary to break it in order to remove the floss and tool. This can be a significant disadvantage, since the floss cannot simply be pulled through the space between the teeth if it should become caught. In addition, even if the floss is under tension when it is molded between the legs of the tool, it tends to stretch and deform in use, and quickly loses tension. Since the floss itself is molded into the ends of the legs of the U-shaped end, there is no way to re-tension the floss extending across the gap between the legs.

Other flossing tools have been developed, which also employ a pair of legs in a U-shaped or wishbone-shaped configuration across which dental floss is stretched. In these tools, floss is not embedded in the plastic legs; but a provision is made for winding a length of floss around an anchor pin or holder, and then extending it through grooves across the opening between the legs and back around the holder. The initial tension can be adjusted by the person applying the floss to the holder. If the floss should become stuck between the teeth, it can be released from the anchor pin and pulled through the teeth; so that such tools are not subject to the disadvantages noted above for tools where the ends of the floss are permanently molded into the legs across the space between the two legs. This tool, however, also is subject to the same disadvantage of the previous tool inasmuch as when the floss is placed under stress, it tends to stretch and become loose and baggy. The floss then must be unwound from the anchor post, pulled tight and re-positioned for further use. This is inconvenient. Frequently, users of such tools find that it is easier simply to wrap the floss around the fingers of two different hands in the conventional manner and floss without the tool.

It is desirable to provide a dental floss tool which is inexpensive, easy to use and which overcomes the disadvantages of the prior art noted above.

SUMMARY OF THE INVENTION

It is an object of this invention to provide an improved dental floss tool.

It is another object of this invention to provide an improved dental floss tool which is reusable.

It is an additional object of this invention to provide a dental floss tool which permits the user to increase the tension on the floss as the tool is used.

It is a further object of this invention to provide an improved dental floss tool which is reusable and which uses short lengths of dental floss guided by the tool across the ends of a pair of extending legs, and in which the path for the floss is such that additional tension can be applied to it by the thumb of the user during use of the tool.

In accordance with a preferred embodiment of the invention, a dental floss tool comprises an elongated handle member with first and second ends. The first end of the handle member terminates in a generally U-shaped extension, with first and second legs joined at one end to the handle member and having the opposite ends thereof spaced apart. A floss winding post is provided on the upper side of the handle member between the first and second ends. A hole is formed through the handle between the floss winding post and the U-shaped extension on the first end of the handle. A provision is made for guiding dental floss from the winding post to the end of the first leg, and from the end of the first leg to the second leg, and, finally, from the end of the second leg back through the hole to the winding post. The length of dental floss between the end of the second leg and the hole is located to permit tensioning of the floss by the thumb of the user.

BRIEF DESCRIPTION OF THE DRAWING

FIG. 1 is a perspective view of a typical prior art dental floss tool;

FIG. 2 is an end view of the tool shown in FIG. 1;

FIG. 3 is a top view of the tool shown in FIG. 1;

FIG. 4 is top perspective view of a preferred embodiment of the invention.

FIG. 5 is a cross-sectional side view of the tool shown in FIG. 4 taken along the line 5—5 of FIG. 4;

FIG. 6 is a diagrammatic representation of the manner of winding dental floss on the tool of FIG. 4; and FIG. 7 is a side view of the tool of FIG. 4, showing its position in use.

DETAILED DESCRIPTION

Reference now should be made to the drawing, in which the same reference numbers are used in the different figures to designate the same components.

FIGS. 1 through 3 show a typical disposable dental floss tool of the type known in the prior art. This tool comprises an elongated handle 10 with a pair of downwardly extending legs 11 and 14 at one end, and with a toothpick-like point 17 at the other end. The tool itself is made of molded plastic and is relatively thin in the transverse direction to the plane of the handle 10 and legs 11 and 14.

In the manufacture of the tool shown in FIGS. 1, 2 and 3, a short length of dental floss 16 is placed in the mold between the free ends of the legs 11 and 14, and is molded in place as shown in FIG. 1. Consequently, the short strip of floss 16 is securely held between the ends of the legs 11 and 14 at all times during the use of the tool. If the floss 16 should break, the tool no longer can be used and must be thrown away.

FIGS. 4 through 7 are directed to a preferred embodiment of a dental floss tool made in accordance with this invention. The tool itself consists of an elongated flat handle 20 which, as illustrated in these figures, is shown in a generally horizontal position. The upper and lower surfaces or sides of the handle 20 are parallel to one another, and its width is greater than the thickness between the upper and lower surfaces, as is most readily apparent by an examination of FIGS. 4 and 5.

A dental floss winding post 22 is secured to the upper surface of the handle 20, as illustrated. This post 22 may be integrally molded with the handle 20 of the same plastic used to form the handle 20, or it may be made a separate part, which then is secured in a hole in the handle 20, as illustrated in FIG. 5. As is apparent from an examination of FIGS. 4 and 5, this post 22 is approximately half-way between the rear end of the handle 20 (the left-hand end as viewed in FIG. 4) and the front end.

The front end of the handle 20 terminates in a downwardly extending generally U-shaped extension in the form of a pair of legs 26 and 27, as is readily apparent in all of FIGS. 4, 5, 6 and 7. It should be noted that the plane of the legs 26 and 27 is perpendicular to the plane of the upper and lower surfaces of the handle 20, which provides a comfortable grip for the hand of a person using the dental floss tool, and facilitates orientation of the tool, by feel, as it is being used. As shown clearly in all of between the floss winding post 22 and the rear leg 26 of the pair of legs 26 and 27.

When the tool is to be used, a short strip of dental floss is wound with a couple of turns around the post 22, as illustrated in FIG. 6. The free end of the floss then is extended downwardly through the hole 24 and through a groove 32 in the end of the leg 26. From this position the floss, as shown in FIG. 6, is extended to a groove 30 in the end of the leg 27 and extending along its outer curved edge back toward the floss winding post 22, where it is wound around the post 22 for two more turns. When this is done, the floss is securely wound in place, as shown in dotted lines in FIG. 5.

It should be noted that the floss winding post 22 is undercut on its lower surface; so that when the floss 40 is wound around the post, the floss tends to wedge between the under side of the post 22 and the upper side or upper surface of the handle 20 to securely hold the floss in place.

As is apparent from an examination of FIG. 5, the floss 40, which extends between the hole 24 and the free end of the rear leg 26 of the pair of legs 26 and 27, forms the hypotenuse of a triangle, the other two sides of which constitute the leg 26 and a portion of the handle 20 between the hole 24 and the leg 26. As the tool is used, if the floss should stretch and become loose, the person using the tool then may place his or her thumb in the position shown in FIG. 7 to press the floss 40 stretched between the hole 24 and the free end of the leg 26 toward the handle 20. This causes the floss 40 to be re-tensioned; so that it is not necessary to unwind it and then rewind it in order to effect the desired tensioning. As illustrated in FIG. 7, the thumb is pressed all of the way into the bite or junction between the handle 20 and the leg 26; but, obviously, intermediate positions between the one shown in FIG. 5 and FIG. 7 may be employed to maintain the desired tension on the floss extending between the free ends of the legs 26 and 27.

It also should be noted that while the floss is shown wound in FIG. 6 by going around the floss winding post 22 first and then through the hole 24, a reverse order of winding from the arrows shown in FIG. 6 also may be effected without changing in any way the use of the tool. Whether the initial direction is over the leg 27 and then across the leg 26 and up through the hole 24 or in the direction shown in FIG. 6, is not important.

The tool itself may be made of any suitable material. A variety of presently available plastics typically are used.

The location of the hole 24 with respect to the winding post 22 and the leg 26 may be varied somewhat; although the location should be such that the application of tension to the floss 40 by the thumb, as illustrated in FIG. 7, readily may be effected in a normal use of the tool. If the floss 40 which extends between the free ends of the legs 26 and 27 should become caught between two adjacent teeth, the free end of the floss which extends from the winding post 22 may be unwound to permit the floss to be pulled out from between the teeth. It is not necessary to break the floss in order to remove it in the event it should become caught.

The foregoing description of the preferred embodiment of the invention should be considered as illustrative and not as limiting. Various changes and modifications will occur to those skilled in the art, without departing from the true scope of the invention as defined in the appended claims.

I claim:

1. A dental floss tool including in combination:
   an elongated handle member having an upper side and a lower side and having first and second ends, said first end terminating in a generally U-shaped extension with first and second legs with a space therebetween extending from the lower side of said handle member, said first leg extending from the first end of said handle member and said second leg located intermediate the first and second ends of said handle member;
   a floss winding post on the upper side of said handle member between the first and second ends thereof;
   a hole through said handle member between said floss winding post and said second leg of said U-shaped extension on the first end of said handle member, with the hole through the handle being located intermediate the floss winding post and the second leg of said U-shaped extension; and
   means on said first and second legs of said U-shaped extension for guiding dental floss from said winding post to the end of said first leg, from the end of said first leg to the end of said second leg across said space, and from the end of said second leg through the hole in said handle member back to said floss winding post, so that the tension of dental floss extending across the space between the ends of said first and second legs may be adjusted by the thumb of a person pressing on the floss between the hole through said handle member and said second leg of said U-shaped extension.

2. The combination according to claim 1 wherein said first and second legs of said U-shaped extension lie in a plane passing through a center line of said elongated handle member.

3. The combination according to claim 2 wherein said elongated handle member is a generally flat handle with the upper and lower sides thereof located in parallel planes, and having a thickness less than the width thereof, and wherein said U-shaped extension comprising said first and second legs is located in a plane perpendicular to the planes of the upper and lower sides of said handle member.

4. The combination according to claim 3 wherein said floss winding post extends outwardly from said handle member and is undercut to accommodate dental floss wound thereabout.

5. The combination according to claim 1 wherein said floss winding post extends outwardly from said handle member and is undercut to accommodate dental floss wound thereabout.

6. The combination according to claim 1 wherein said elongated handle member is a generally flat handle with the upper and lower sides thereof located in parallel planes, said having a thickness less than the width thereof, and wherein said U-shaped extension comprising said first and second legs is located in a plane perpendicular to the planes of the upper and lower sides of said handle member.

7. The combination according to claim 1 wherein said U-shaped extension on said first end of said handle member is located such that said second leg of said U-shaped extension is located between the first leg of said U-shaped extension and said second end of said handle member.

* * * * *